United States Patent
Deusser et al.

[11] Patent Number: 5,415,936
[45] Date of Patent: May 16, 1995

[54] SURFACE-MODIFIED PYROGENICALLY PRODUCED TITANIUM DIOXIDE

[75] Inventors: Hans Deusser, Karlstein; Dieter Kerner, Hanau; Jürgen Meyer, Stockstadt; Günther Michael, Karlstein; Andreas Stubbe, Rodenbach, all of Germany

[73] Assignee: Degussa Aktiengesellschaft, Frankfurt, Germany

[21] Appl. No.: 12,160

[22] Filed: Jan. 28, 1993

[30] Foreign Application Priority Data

Jan. 31, 1992 [DE] Germany .................. 42 02 695.4

[51] Int. Cl.$^6$ .................................................. B32B 1/00
[52] U.S. Cl. .................................. 428/405; 428/402; 428/403; 428/447
[58] Field of Search ........... 428/403, 402, 447, 689, 428/702, 404, 405; 430/110

[56] References Cited

U.S. PATENT DOCUMENTS

| | | | |
|---|---|---|---|
| 4,618,556 | 10/1986 | Takenouchi | 430/110 |
| 4,828,954 | 5/1989 | Hashimoto et al. | 430/110 |
| 4,845,004 | 7/1989 | Kobayashi | 430/110 |
| 4,943,506 | 7/1990 | Demizu et al. | 430/109 |
| 5,026,620 | 6/1991 | Masaki et al. | 430/99 |
| 5,102,763 | 4/1992 | Winnik et al. | 430/110 |
| 5,192,637 | 3/1993 | Saito et al. | 430/109 |

OTHER PUBLICATIONS

German Office Action dated Nov. 9, 1992.
English Translation of German Office Action.
Chemical Abstract, vol. 102 (8) Nr. 70140u.
Chemical Abstract, vol. 113 (20) Nr. 181399g.
Chemical Abstract, vol. 100 (22) Nr. 183164g.

*Primary Examiner*—Patrick J. Ryan
*Assistant Examiner*—Marie R. Macholl
*Attorney, Agent, or Firm*—Cushman, Darby & Cushman

[57] ABSTRACT

Surface-modified, pyrogenically produced titanium dioxide which has the following physico-chemical properties:

| | | |
|---|---|---|
| Surface | (m$^2$/g) | 5 to 120 |
| Stamping density | (g/l) | 50 to 250 |
| Drying loss | (%) | <5 |
| Annealing loss | (%) | 3.5 to 15 |
| Carbon content | (%) | 0.5 to 12 |
| pH | | 4 to 10. |

3 Claims, 1 Drawing Sheet

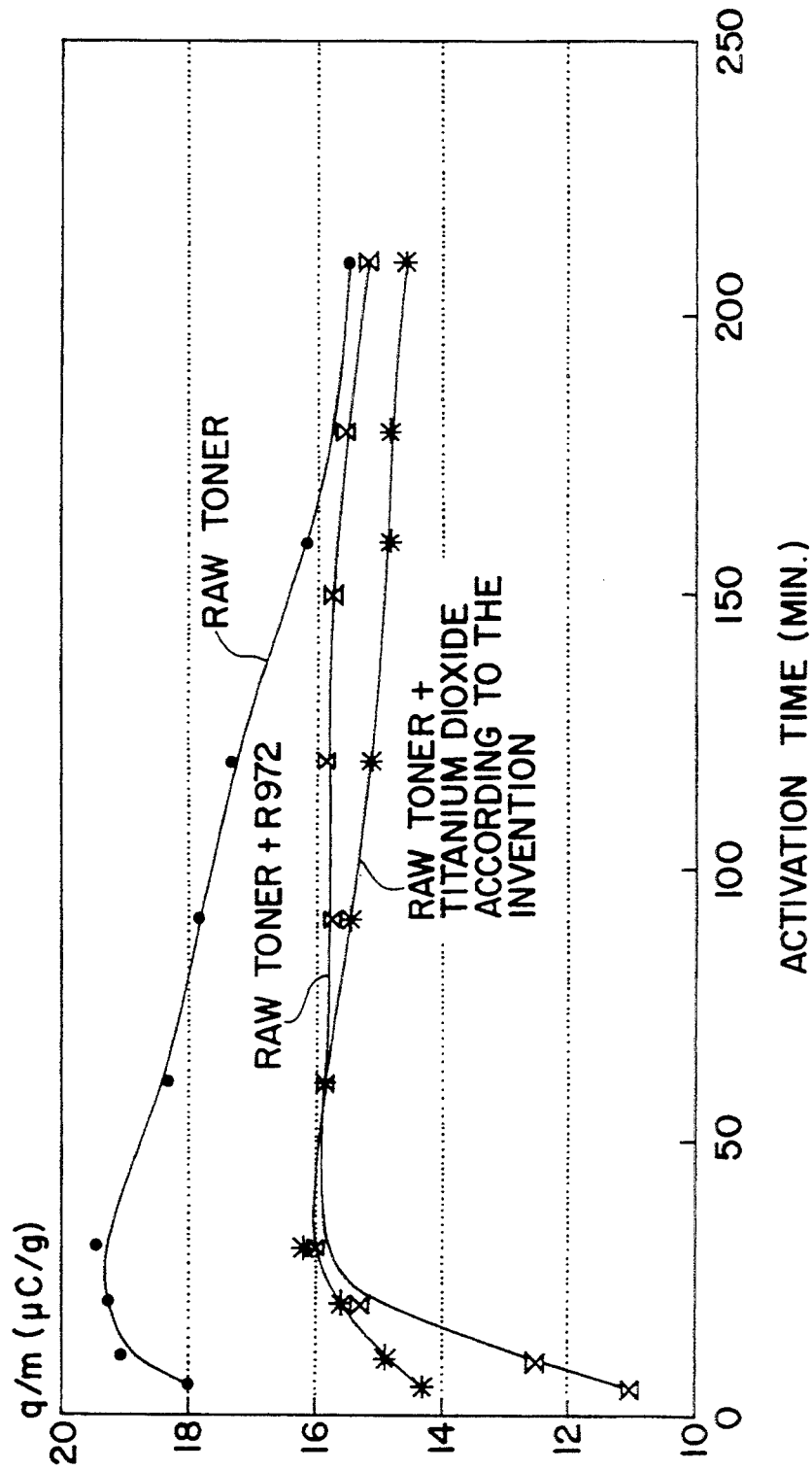

SURFACE-MODIFIED PYROGENICALLY PRODUCED TITANIUM DIOXIDE

The present invention relates to a surface-modified, pyrogenically produced titanium dioxide.

BACKGROUND OF THE INVENTION

It is known to use powdery toners containing surface-modified pyrogenically produced silicon dioxide in electrostatic developing processes. Various silanes, especially dimethyldichlorosilane, are used for surface modification (See U.S. Pat. No. 3,720,617).

It is also known that pyrogenically produced silicon dioxide waterproofed with compounds of the general formula

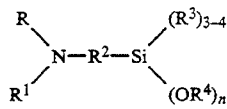

can be added to positively chargeable resin powders in order to increase their flowability (See published European Patent Application EP-A 0,293,009).

It also is known that a titanium dioxide which has been surface-modified with halogen silanes can be added to electrographic developing powders (See published German patent application DE-A 12 09 427).

Furthermore, Published German Patent Application DE-A 34 26 685 (Canon) teaches the addition of a titanium dioxide to positively chargeable toners in which the titanium dioxide had been treated with simultaneously with the adhesion promoters γ-aminopropyl-triethoxysilane and trimethylethoxysilane.

A similarly treated titanium dioxide is described in Published Japanese Patent Application JP-OS 31442 (Nippon Aerosil Corporation).

The known method has the disadvantage that it must use an organic solvent system. Alcohols, hydrocarbons and halogenated hydrocarbons are used as solvents which cannot be completely removed from the reaction product.

SUMMARY OF THE INVENTION

The object of the present invention is to avoid these problems and produce a solvent-free, waterproofed titanium dioxide.

The present invention provides a surface-modified, pyrogenically produced titanium dioxide which is surface modified with a silane mixture consisting of silane A (trimethoxyoctylsilane) and silane B (3-aminopropyl-triethoxysilane) having the following chemical formulas:

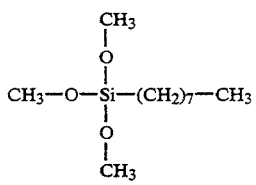

Silane A

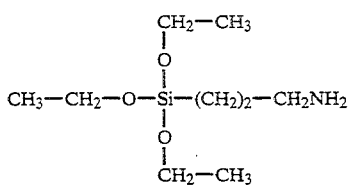

Silane B

The surface-modified, pyrogenically produced titanium dioxide has the following physico-chemical characteristics:

| Surface | (m$^2$/g) | 5 to 120 |
|---|---|---|
| Stamping density | (g/l) | 50 to 250 |
| Drying loss | (%) | <5 |
| Annealing loss | (%) | 3.5 to 15 |
| Carbon content | (%) | 0.5 to 12 |
| pH | | 4 to 10. |

The present invention also provides a method of producing the surface-modified, pyrogenically produced titanium dioxide in which the pyrogenically produced titanium dioxide is placed in a mixer and sprayed, with the mixer running, with a mixture of silanes A and B. The silanes and the pyrogenically produced titanium dioxide are mixed after the addition of the silane mixture, and the resulting mixture is tempered at 100° to 150 ° C., preferably at 115° to 125 ° C.

The ratio of titanium dioxide to silane mixture can be 0.5 to 40 parts by weight silane mixture per 100 parts by weight titanium dioxide.

The silane mixture can consist of 1 to 99 parts by weight silane A and 99 to 1 parts by weight silane B.

A mixture can be used with preference consisting of 50±20 parts by weight silane A and 50±20 parts by weight silane B.

A particularly suitable titanium dioxide is P 25 which has been produced pyrogenically from TiCl$_4$ by flame hydrolysis, in an oxyhydrogen flame, and which has the following physico-chemical characteristics:

| | | Titanium dioxide P 25 |
|---|---|---|
| Behavior vis-à-vis water | | hydrophilic |
| Appearance | | loose white powder |
| Surface according to BET[1] | m$^2$/g | 50 ± 15 |
| Average size of the primary particles | nm | 21 |
| Stamping density[2] | g/l | ca. 100 |
| Specific weight[10] | g/ml | ca. 3.7 |
| Drying loss[3] (2 hours at 105° C.) | % | <1.5 |
| Annealing loss[4][7] (2 hours at 1000° C.) | % | <2 |
| pH[5] (in 4% aqueous dispersion) | | 3–4 |
| SiO$_2$[8] | % | <0.2 |
| Al$_2$O$_3$[8] | % | <0.3 |
| Fe$_2$O$_3$[8] | % | <0.01 |
| TiO$_2$[8] | % | >99.5 |
| ZrO$_2$[9] | % | — |
| HfO$_2$[8] | % | — |
| HCl[8][9] | % | <0.3 |
| Sieve residue[6] (according to | % | <0.05 |

|  | Titanium dioxide P 25 |
|---|---|
| Mocker, 45 μm) | |

[1] according to DIN 66 131
[2] according to DIN ISO 787/XI, JIS K 5101/18 (non-sieved)
[3] according to DIN ISO 787/II, ASTM D 280, JIS K 5101/21
[4] according to DIN 55 921, ASTM D 1208, JIS K 5101/23
[5] according to DIN ISO 787 IX, ASTM D 1208, JIS K 5101/24
[6] according to DIN ISO 787/XVIII, JIS K 5101/20
[7] relative to the substance dried 2 hours at 105° C.
[8] relative to the substance annealed 2 hours at 1000° C.
[9] HCl content is a component of the annealing loss The waterproofed titanium dioxide of the invention has the advantage that it has no solvent components. It can be used in toners for copiers.

BRIEF DESCRIPTION OF FIGURE OF DRAWING

In the drawing:

FIGURE 1 is a graph which plots the q/m values of samples of toner.

DETAILED DESCRIPTION OF PREFERRED EMBODIMENTS

The following examples illustrate the invention:

EXAMPLE 1

2 kg P 25 $TiO_2$ produced pyrogenically from $TiCl_4$ in an oxyhydrogen flame and exhibiting the data indicated above are placed in a 135 liter Lodige mixer and sprayed with 100 g of a silane mixture consisting of 50 g trimethoxyoctylsilane and 50 g 3-aminopropyltriethoxysilane with the mixer running. The mixture is mixed for an additional 15 minutes. The silanized oxide is tempered for 2 hours at 120° C.

The physico-chemical properties of the surface-modified titanium dioxide are as follows:

| Carrier | | $TiO_2$ |
|---|---|---|
| Surface | (m²/g) | 38 |
| Stamping density | (g/l) | 134 |
| Drying loss | (%) | 0.2 |
| Annealing loss | (%) | 3.5 |
| C content | (%) | 3.0 |
| pH | | 8.2 |

EXAMPLE 2

The titanium dioxide waterproofed according to Example 1 is tested in a positive toner system. The toner system consists of the following components:

| Pigment black Printex 35 | 7% |
|---|---|
| Copy-Blau PR (Hoechst AG) | 3% |
| Toner resin | 90% |

The repeated activation was tested with this toner system and a high charge stability in comparison to the raw toner was found (see FIGURE 1).

Copy-Blau PR is a charge regulating agent for positive toners. It is characterized as follows:

Area of application:
1. Charge regulating agents for positive toners (1- or 2-component toners for copiers or laser printers)
2. Clearing agents for black toners Chemical characterization: triphenylmethane derivative
Thermal resistance: >200 C.
Solubility:
    insoluble in water
    slightly soluble in organic solvents The toner resin used is characterized as follows:

| | Unit | Theoretical value |
|---|---|---|
| Melt flow Index[1] (150° C./2, 16 kp) | g/10 min | 5–10 |
| Viscosity number[2] | cm³/g | 37–43 |
| Weight loss[3] | % by weight | <1 |
| Residual monomers[4] | % by weight | <0.35 |
| Styrene | | <0.25 |
| N-BMA | | <0.10 |
| Other product properties: | | |
| Monomer composition | 70% by weight styrene | |
| | 30% by weight n-butylmethacrylate | |
| Glass transition temperature Tg[5] | 60–65° C. | |
| Average grain diameter[6] (d 50% RS) | 0.200–0.314 mm | |

[1] DIN 53 735, 2/88 edition
Specimen pretreatment: Drying at 50 C. oil pump vacuum, 1 hour or 4 hours drying oven, 50° C.
[2] DIN 7745, 1/80 edition.
[3] IR drier until weight constancy
[4] Gas chromatography
[5] DSC method, ASTM D 3418/75
[6] DIN 53 734, 1/73 edition, evaluation according to DIN 66 141, 2/74 edition The pigment black Printex 35 is characterized as follows:
RCF (regular color furnace)
Density: (g/cm³) 1.8–1.9
Product specifications

| Printex 35 RCF | Class | Depth of Color M$_y$-value | Color Strength IRB 3 = 100 | DBP Adsorption (mg/100 g) powder beads | | Volatile Components (%) | pH | Extract contents toluene (%) | Sieve Residue (%) |
|---|---|---|---|---|---|---|---|---|---|
| | | | | Powder | Beads | | | | |
| Furnace Blacks Printex 35 | RCF | 236 | 100 | 42 | 42 | 0.9 | 9.5 | <0.1 | 0.05 |

| | Further technical data | | | |
|---|---|---|---|---|
| | Ashing Residue | Stamping Density | | Particle Size (nm) | BET Surface (m²/g) |
| | | Powder | Beads | | |
| Furnace Blacks Printex 35 | 0.3 | 420 | 550 | 31 | 65 |

The q/m measurement takes place under the following conditions:

98% carrier (spherical ferrite (80–100 m))

2% titanium dioxide according to example 1

Activation: Rolling fixture, 360 rpms in 40 ml glass bottle, weighed portion 40 g, developer

What is claimed is:

1. A pyrogenically produced titanium dioxide which has been surface modified with a mixture of silane A and silane B corresponding to the chemical formulas:

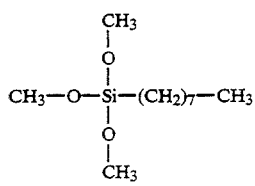

Silane A

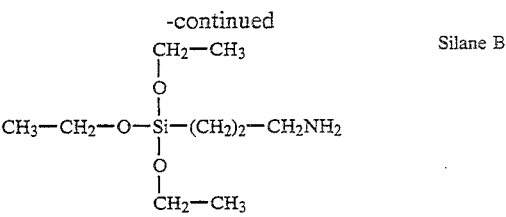

Silane B said surface-modified, pyrogenically produced titanium dioxide having the following physico-chemical properties:

| | | |
|---|---|---|
| Surface | (m²/g) | 5 to 120 |
| Stamping density | (g/l) | 50 to 250 |
| Drying loss | (%) | <5 |
| Annealing loss | (%) | 3.5 to 15 |
| C content | (%) | 0.5 to 12 |
| pH | | 4 to 10. | wherein the ratio of titanium dioxide to silane mixture is 0.5 to 40 parts by weight of silane mixture per 100 parts by weight titanium dioxide.

2. A surface modified pyrogenically produced titanium dioxide as set forth in claim 1 in which the silane mixture contains 1 to 99 parts by weight of silane A and 1 to 99 parts by weight of silane B.

3. A pyrogenically-produced titanium dioxide as set forth in claim 2 in which the silane mixture contains 50±20 parts by weight of silane A and 50±20 parts by weight of silane B.

* * * * *